US011439724B2

United States Patent
Thuleau et al.

(10) Patent No.: US 11,439,724 B2
(45) Date of Patent: Sep. 13, 2022

(54) DEVICE FOR ADSORBING ODOURS (71) Applicants: Institut Curie, Paris (FR); Ecole Superieure de Physique et de Chimie Industrielle (ESPCI), Paris (FR); Ecole Nationale Superieure de Chimie de Paris (ENSCP), Paris (FR); Centre National de la Recherche Scientifique, Paris (FR); Cemag Care, Paris (FR)

(72) Inventors: Aurélie Thuleau, Levallois Perret (FR); Isabelle Fromantin, Les Ulis (FR); Vincent Semetey, Le Mans (FR); José Dugay, Palaiseau (FR); Jean-François Le Meur, Hede (FR)

(73) Assignees: Institute Curie, Paris (FR); Ecole Superieure De Physique Et De Chimie Industrielle (ESPCI), Paris (FR); Ecole Nationale Superieure De Chimie De Paris (ENSCP), Paris (FR); Centre National De La Recherche Scientifique, Paris (FR); Cemag Care, Paris (FR)

( * ) Notice: Subject to any disclaimer, the term of this patent is extended or adjusted under 35 U.S.C. 154(b) by 169 days.

(21) Appl. No.: 16/909,053

(22) Filed: Jun. 23, 2020

(65) Prior Publication Data
US 2020/0376155 A1 Dec. 3, 2020

Related U.S. Application Data (63) Continuation of application No. 16/320,176, filed as application No. PCT/FR2017/052068 on Jul. 25, 2017, now Pat. No. 10,772,985.

(30) Foreign Application Priority Data

Jul. 26, 2016 (FR) ...................................... 1657156

(51) Int. Cl.
*A61L 15/40* (2006.01)
*A61L 9/012* (2006.01)
(Continued)

(52) U.S. Cl.
CPC ............... *A61L 15/40* (2013.01); *A61L 9/012* (2013.01); *A61L 9/013* (2013.01); *A61L 15/46* (2013.01); *A23L 27/00* (2016.08); *A61L 2300/20* (2013.01)

(58) Field of Classification Search
CPC .......... A61L 15/40; A61L 9/012; A61L 9/013; A61L 15/46; A61L 2300/20; A61L 9/014;
(Continued)

(56) References Cited

U.S. PATENT DOCUMENTS

2003/0004479 A1   1/2003   Ueda et al.
2010/0249737 A1   9/2010   Ito et al.

FOREIGN PATENT DOCUMENTS

CN   104521779 A    4/2015
EP   1 352 927   * 10/2003
(Continued)

*Primary Examiner* — Carlos A Azpuru
(74) *Attorney, Agent, or Firm* — Cesari & McKenna, LLP

(57) ABSTRACT

The invention relates to a device for adsorbing odours comprising an absorbent layer and an adsorbent layer, said adsorbent layer being provided with a material permeable to volatile organic compounds (VOCs) and an adsorbent particulate filler comprising at least one spice. Such a device is particularly useful for adsorbing and masking body odours.

16 Claims, 7 Drawing Sheets

(51) Int. Cl.
*A61L 9/013* (2006.01)
*A61L 15/46* (2006.01)
*A23L 27/00* (2016.01)

(58) Field of Classification Search
CPC ............... A23L 27/00; A61F 13/0003; A61F 2013/00914; A61F 2013/8435; A61F 13/0063
See application file for complete search history.

(56) References Cited

FOREIGN PATENT DOCUMENTS

| | | |
|---|---|---|
| EP | 1352927 A1 | 10/2003 |
| JP | H-293136 A | 11/1993 |
| JP | 2002285021 A | 10/2002 |
| JP | 2008108476 A1 | 9/2008 |
| KR | 1622250 B1 | 5/2016 |

* cited by examiner

DEVICE FOR ADSORBING ODOURS

CROSS-REFERENCE TO RELATED APPLICATIONS

This application is a continuation of U.S. application Ser. No. 16/320,176, filed Jan. 24, 2019, now U.S. Pat. No. 10,772,985, which is the National Stage of International Application No. PCT/FR2017/052068, filed Jul. 25, 2017, which claims the benefit of French Application No. 1657156, filed Jul. 26, 2016. The contents of the prior applications are hereby incorporated by reference in their entirety.

INTRODUCTION

The invention relates to a device for reducing odours, and notably body odours, comprising at least one adsorbent spice. More particularly, the invention relates to a device for medical or paramedical use for adsorbing body odours, such as those emanating from necrosis, pus, defecation, urine, exudates, blood, sweat, etc. The invention also relates to the use of such a device in the form of a dressing, diaper, hygienic protection, absorbent pad or panty liner to adsorb and mask odours. The invention also relates to the use of an adsorbent spice as adsorbent in a device for adsorbing odours.

Many odours are likely to emanate permanently from a human or animal body. Some of these odours may be perceived negatively by the individual from whom they originate and/or those around them. The unpleasant, even repulsive feeling associated with such odours can have a dramatic sociological impact on an individual's life. This is particularly the case for foul odours emanating from chronic wounds, the intensity of which causes considerable discomfort for patients and those around them. To a lesser extent, people with urinary and/or faecal incontinence, or who have had an intestinal or digestive stoma, may also experience discomfort due to foul odours.

Various devices, chiefly based on activated charcoal, have been developed to adsorb odours and improve the quality of life of individuals facing such problems of uncontrollable emanation of odours, the cause of which cannot necessarily be treated quickly. One particular example is a dressing, intended to be applied to a malodorous wound, composed of activated charcoal covered with a non-woven nylon sleeve (Actisorb®). Activated charcoal, although known for its adsorbent properties, is not always satisfactory in the case of very strong odours, such as odours from necrotic, infected or tumour wounds.

Faced with the inability of current devices to satisfactorily control the emanation of foul odours, particularly in certain clinical situations, there is therefore a real need for an alternative (and non-antibiotic) solution to improve the comfort of those likely to emit such odours and those around them.

SUMMARY OF THE INVENTION

While working on this problem, the inventors surprisingly discovered that certain spices have particularly advantageous adsorbent capacities which make it possible to reduce unpleasant odours, and notably odours emanating from malodourous wounds, in a highly satisfactory manner. Moreover, unlike activated charcoal, spices not only adsorb most of the odorous emanations, but also cover or mask those that may not be fully adsorbed. The inventors have thus developed a device incorporating at least one spice, in powder form, which adsorbs odours and, when in contact with or near the source of bad odours, reduces or even eliminates the discomfort of the user, and of those around the user, caused by these odours. This is particularly the case for spices such as cinnamon, turmeric or clove, which, in powder form, have adsorbent and masking properties particularly suitable for eliminating or strongly reducing foul body odours and the discomfort associated with their emanations.

The invention thus relates to an odour adsorption device comprising an absorbent layer and an adsorbent layer, said adsorbent layer being provided with a material permeable to volatile organic compounds (VOCs) and an adsorbent particulate filler comprising at least one spice.

The invention also relates to the use of a spice, preferably cinnamon, as adsorbent in a device for adsorbing odours, especially body odours. The spice is advantageously in powder form.

The invention also relates to the use of an adsorbent layer comprising a material permeable to volatile organic compounds (VOCs) and an adsorbent particulate filler comprising at least one fragrant spice, for adsorbing odours, especially body odours.

DETAILED DESCRIPTION

The invention is chiefly based on the discovery that spices can advantageously replace activated charcoal, widely used today as adsorbent, in a device for adsorbing odours, in order to adsorb and mask odours, and especially body odours. More particularly, the invention proposes to use at least one spice in powder form, and preferably cinnamon, clove and/or turmeric, as adsorbent to reduce odours, notably by integrating the powdered spice(s) into a device intended to be placed in contact with or near a source of foul odours. According to the invention, the spice is integrated into and maintained within the device in powder form.

In the context of the invention, a "spice" refers to a fragrant substance of plant origin.

The principle of adsorption is a surface phenomenon by which atoms or molecules of gas or liquid adhere to a solid, adsorbent surface. In the context of the invention, "adsorbent" refers to the ability to bind volatile organic compounds (VOCs), so that few if any of these VOCs spread in the air. Odours associated with the emanation of these VOCs are thus reduced or even eliminated. More particularly, an "adsorbent spice" is defined as a spice which, in powder form, is capable of adsorbing at least 20%, 30%, 40%, preferably at least 50%, more preferably at least 60% of at least one VOC among dimethyl disulphide (DMDS), phenol (Ph) and indole (In). In the context of the invention, the percentage or rate of adsorption of a spice is measured by depositing said spice in a tube containing the VOCs and by reference to a control tube also containing the 3 VOCs but not containing any spices, according to the formula:

adsorption rate=[(control tube VOC peak area)−(spice tube VOC peak area)]/(control tube VOC peak area)

According to the invention, chromatographic profiles are obtained by a chromatographic method coupling headspace solid-phase microextraction (HS-SPME) to gas chromatography (GC) associated with mass spectrometry (MS) detection (HS-SPME-GC-MS coupling) (Preti et al., Journal of Chromatography B 2009; vol. 877, pp. 2011-2018; Rey et al., International Journal of Greenhouse Gas Control 2013, vol. 19, no. 11, pp. 576-583).

"Particulate filler", or "powder", refers to a solid material in the form of macroscopic particles. According to the invention, the particulate filler comprises or consists of a spice, in the form of a powder with a particle size advantageously less than 500 μm.

"Particle size" refers to the particle size distribution of the particulate filler, and more particularly of the spice, concerned. The particle size may notably be measured by dry sieving, wet sieving, sedimentometry, laser diffraction, microscopy, etc. The average particle size is the average particle diameter calculated from a volume distribution. More precisely, the arithmetic mean diameter ($d_a$) was calculated, for a sample fractionated into n classes of representative diameters $d_i$, according to the formula:

$$d_a = D(4,3) = \frac{\sum_{i=1}^{n} d_i^4 N_i}{\sum_{i=1}^{n} d_i^3 N_i}$$

-continued $i$ = particle class, $N_i$ = number or percentage of particles in the class In one embodiment, the particulate filler consists of a spice powder with an average particle size of less than 1000 μm, 900 μm, 800 μm, 700 μm, 600 μm, 500 μm, 400 μm, 300 μm, 200 μm, 150 μm, 100 μm, 90 μm, 80 μm, 70 μm, 60 μm, 50 μm, 40 μm. In particular, the particulate filler may be comprised between 10 μm and 1000 μm, 700 and 900 μm, 800 and 900 μm, 40 and 400 μm, between 50 and 380 μm, between 40 and 100 μm, between 50 and 60 μm. For example, the particulate filler has an average particle size of 52 μm, ±10%. In one embodiment, the average particle size of the particulate filler is not less than 70 μm, 80 μm, 90 μm, 100 μm, 150 μm. In one example, the particulate filler has a particle size comprised between 60 and 100 μm. In another example, the particulate filler has an average particle size of 90 μm, ±10%. In another embodiment, the average particle size of the particulate filler is not less than 700 μm, 750 μm, 800 μm, 850 μm, 900 μm. In one example, the particulate filler has a particle size comprised between 800 and 900 μm, preferably between 800 and 850 μm. In another example, the particulate filler has an average particle size of 850 μm, ±10%.

According to the invention, the given particle size corresponds to the particle size obtained with the Beckman Coulter LS 13320 laser particle size analyser (Beckman Coulter, USA) using air as solvent.

The inventors have shown that spices, and more particularly spices in powder form, are able to adsorb a large number of potentially malodorous VOCs so as to reduce the nauseating impression associated with their presence. Interestingly, these spices can also mask VOCs by the presence of their own VOCs, the smell of which can overpower the others.

Preferably, the particulate filler of the adsorbent layer of the device according to the invention comprises cinnamon, clove and/or turmeric powder, more preferably cinnamon.

In a particular embodiment, the particulate filler of the adsorbent layer of the device according to the invention comprises cinnamon powder or turmeric powder with a particle size comprised between 40 and 100 μm, 60 and 100 μm, or 80 and 90 μm, ±10%. Advantageously, the particulate filler of the adsorbent layer of the device according to the invention comprises cinnamon powder with a particle size comprised between 50 and 60 μm. In particular, the particulate filler of the cinnamon powder has an average particle size of 52 μm, ±10%.

In a particular embodiment, the particulate filler of the adsorbent layer of the device according to the invention comprises clove powder with a particle size comprised between 10 and 1000 μm. In a particular embodiment, the clove powder has a particle size comprised between 800 and 900 μm, preferably between 800 and 850 μm, ±10%.

In one embodiment, the device comprises between 0.1 and 10 g of spices per 100 cm² of VOC-permeable material, preferably between 0.3 and 5 g, even more preferably between 0.5 and 2 g, between 0.5 and 1.5 g, between 0.5 and 1 g. For example, the device comprises between 0.5 and 1.5 g of cinnamon per 100 cm² of VOC-permeable material, and notably about 0.9 g of cinnamon per 100 cm² of VOC-permeable material. In one embodiment, the device comprises between 0.1 and 2 g, preferably between 0.3 and 1.5 g, more preferably between 0.5 and 1 g of spices per 100 cm² of VOC-permeable material. In one embodiment, the device comprises between 1 and 4 g, preferably between 2 and 3 g, more preferably 2 g of spices, and notably of cinnamon, per 100 cm² of VOC-permeable material.

The VOC-permeable material of the adsorbent layer may be any woven or non-woven fabric. For example, the VOC-permeable material of the adsorbent layer is nylon (poly(hexamethylene adipamide)), cotton, linen, viscose, polyethylene, polypropylene and/or polyester. Advantageously, the particulate filler is embedded in and/or interweaved between the fibres of the woven or non-woven fabric.

In a particular embodiment, the VOC-permeable material of the adsorbent layer is a fabric having geometric shapes, such as a grid, cells, a quilt, obtained notably by topstitching, welding, gluing, etc. of the fabric or by virtue of the very weft of said fabric. Advantageously, the shapes are evenly distributed over the entire surface of the fabric and form compartments in whose volume the particulate filler is retained independently of the site of use or gravity.

In a particular embodiment, the fabric consists of cells (such as a honeycomb fabric). In another exemplary embodiment, the fabric consists of a grid. Thus, regardless of the position of the adsorbent layer in relation to the user, the particulate filler is maintained in the compartments and remains evenly distributed over the entire surface of the fabric. More particularly, the use of such a compartmentalized fabric prevents clumps of powder from forming heterogeneously, in particular in the corners or in part of the device when handled and/or used, notably due to gravity. The device according to the invention is particularly suitable for adsorbing body odours, and notably in the context of medical and paramedical uses, for adsorbing odours that may emanate from body fluids, such as exudates, urine, defecations, etc. The device according to the invention is particularly suitable for adsorbing odours emanating from chronic wounds, and notably from tumour wounds from which a very large number of malodorous VOCs emanate, such as organosulphur compounds (such as dimethyl disulphide DMDS, dimethyl trisulphide DMTS), phenols and indoles.

According to the invention, the device includes an absorbent layer, intended to absorb the liquid or moisture which may be present in the environment from which the bad odours emanate. Thus, only the VOCs pass through all or part of this first layer and are captured by the second adsorbent layer, the adsorbent properties of which are therefore not affected by the presence of liquid.

Any non-occlusive absorbent material may be used for this first layer. In one embodiment, the absorbent layer comprises at least one permeable or semi-permeable material, preferably selected from alginates, viscose, carboxymethylcellulose (CMC), hydrophilic cotton or cellulose, hydrogels such as sodium polyacrylate, polyvinyl pyrrolidine, collagen, hyaluronic acid, chitosan, alginate, gelatine, and sponges or foam such as polyurethane foam or composites of these materials.

For example, the device according to the invention may be a dressing, diaper, sanitary protection, pad or panty liner. The absorbent layer is thus intended to be in contact with the source of body fluid in order to at least partially absorb moisture. The device according to the invention may also be a "secondary dressing", intended to be affixed to a dressing itself in direct contact with the source of body fluid. In such an embodiment, the device according to the invention does not come into direct contact with the source of body fluid.

In one embodiment, the device further comprises a protective layer, preferably semi-permeable or impermeable to moisture, arranged so that it is sandwiched between the absorbent layer and the adsorbent layer. In particular, the protective layer prevents the exudates from reaching the adsorbent layer and, conversely, the spices from diffusing towards the absorbent layer, and the adsorbent layer from being contaminated by external liquids. Such a protective layer may notably be a woven or non-woven fabric, a film or a microporous membrane. In a particular embodiment, the protective layer is composed of a material preferably selected from polyethylene, polypropylene, polyurethane, polyester, polyamide, polydimethylsiloxane, fluoropolymers and/or composites of these materials.

The invention relates to a dressing comprising a particulate filler based on cinnamon. The dressing comprises a first absorbent layer intended, for example, to be applied to a chronic wound, such as a tumour wound, and a second adsorbent layer consisting of a woven or non-woven fabric comprising cinnamon powder, preferably with a particle size comprised between 80 and 90 µm, ±10%. Preferably, such a device comprises between 0.5 and 2 g, preferably between 1 and 1.5 g, of cinnamon per 100 cm² of VOC-permeable material. The invention also relates to a dressing comprising a first absorbent layer intended, for example, to be applied to a chronic wound, such as a tumour wound, and a second adsorbent layer consisting of a woven or non-woven fabric comprising cinnamon powder, with a particle size comprised between 50 and 60 µm, notably equal to 52 µm±10%, said device comprising between 1 and 4 g, and notably about 2 g of cinnamon per 100 cm² of VOC-permeable material.

The invention also relates to a dressing comprising a particulate filler based on clove. The dressing comprises a first absorbent layer intended, for example, to be applied to a chronic wound, such as a tumour wound, and a second adsorbent layer consisting of a woven or non-woven fabric comprising clove powder, preferably with a particle size comprised between 10 and 1000 µm, and notably between 800 and 900 µm, more preferably between 800 and 850 µm ±10%, for example about 820 µm. Preferably, such a device comprises between 0.5 and 2 g, or between 1 and 4 g, preferably between 1 and 1.5 g, or between 2 and 3 g of clove per 100 cm² of VOC-permeable material.

In a particular embodiment, the adsorbent layer comprises between 0.5 and 5 g, preferably between 1 and 4 g, more preferably 2 g of spices per 100 cm² of VOC-permeable material.

The invention also relates to a dressing comprising a particulate filler based on turmeric, and notably based on Curcuma longa. The dressing comprises a first absorbent layer intended, for example, to be applied to a chronic wound, such as a tumour wound, and a second adsorbent layer consisting of a woven or non-woven fabric comprising turmeric powder, preferably with a particle size comprised between 50 and 150 µm, preferably between 80 and 100 µm, more preferably equal to 90 µm±10%. Preferably, such a device comprises between 0.5 and 2 g, preferably between 1 and 1.5 g, of turmeric per 100 cm² of VOC-permeable material.

The invention also relates to a dressing comprising a particulate filler based on turmeric as described above, in which the particle size of the turmeric powder is comprised between 50 and 150 µm, preferably between 80 and 100 µm, more preferably equal to 90 µm±10%, said device comprising between 1 and 4 g, and notably about 2 g of turmeric per 100 cm² of VOC-permeable material.

Figure 1:
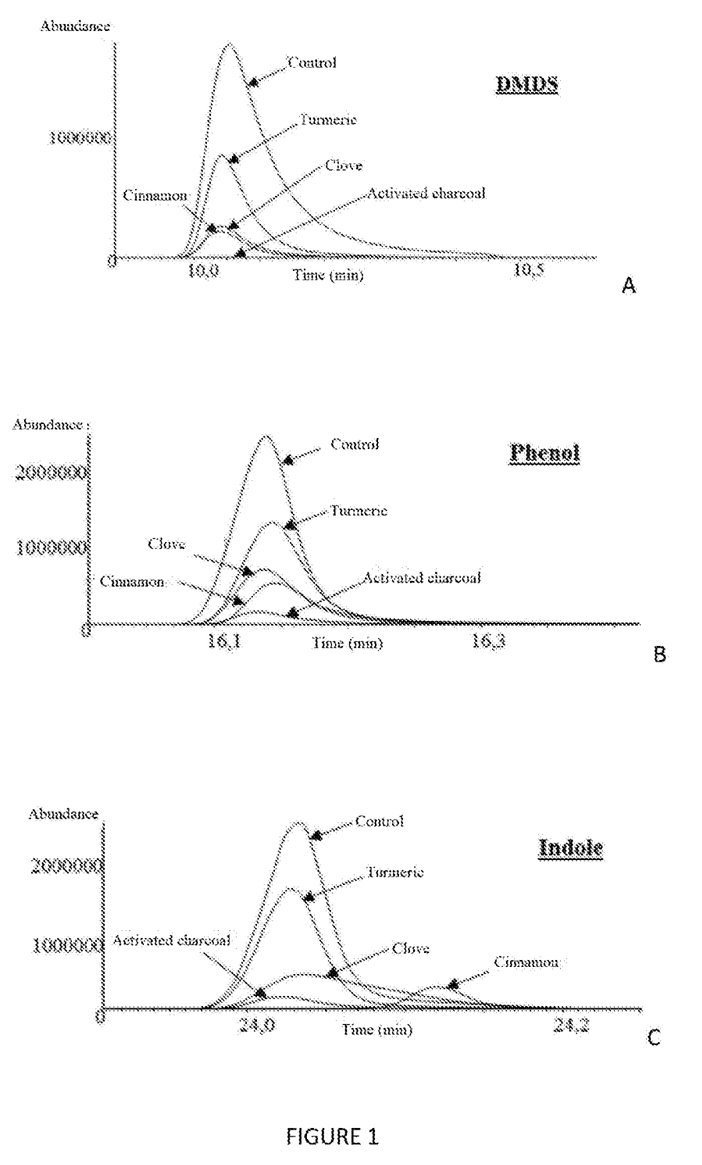
FIG. 1: Comparison of the adsorbent properties of activated charcoal (Actisorb®), cinnamon powder, turmeric powder and clove powder, which may be used in the device according to the invention, on three VOCs characteristic of malodorous necroses, dimethyl disulphide—DMDS (A), phenol-Ph (B) and indole—In (C), the Control representing the VOC concerned (100% abundance)
Figure 2:
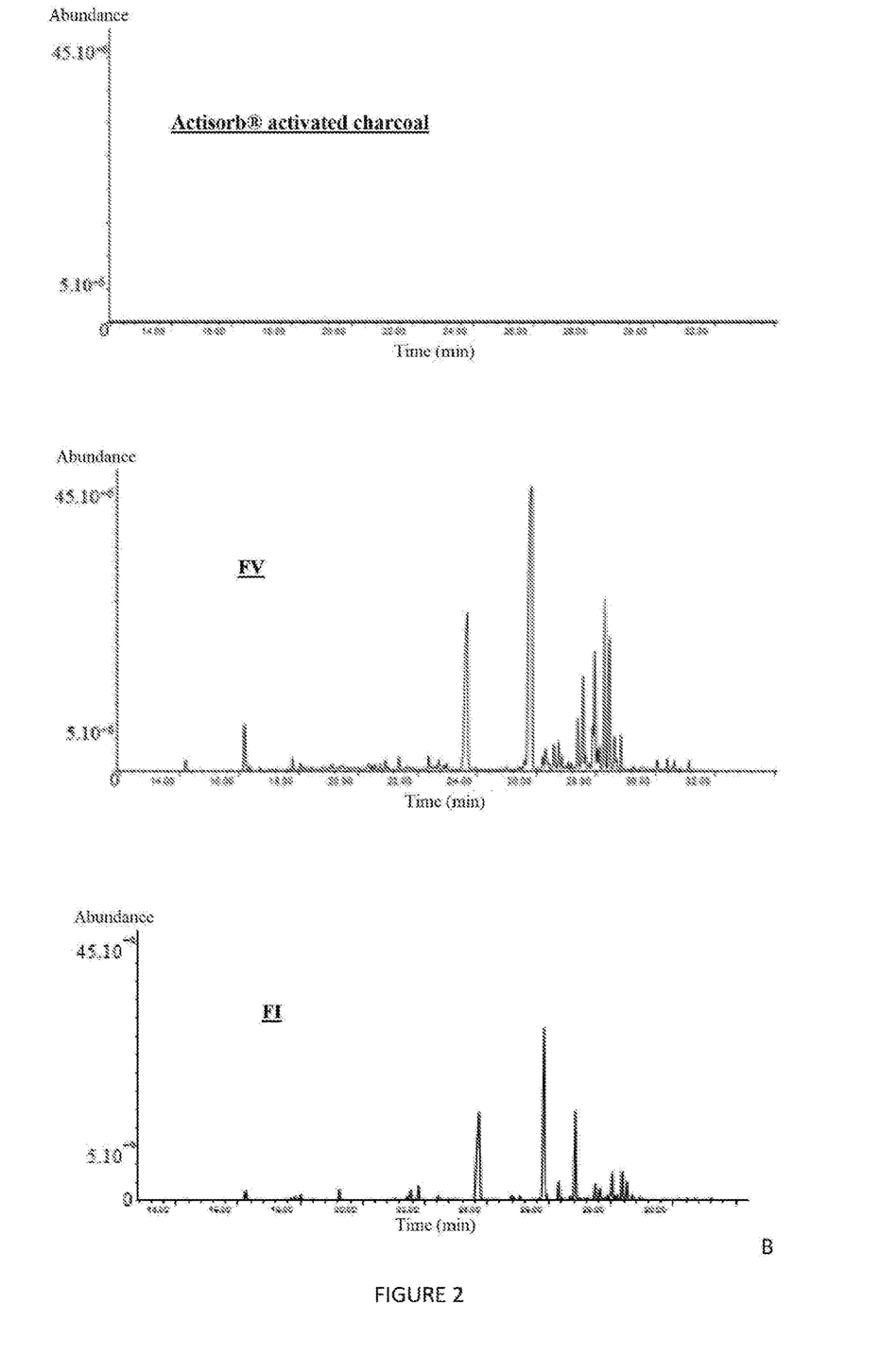
FIG. 2: Comparison of the VOCs emitted by (A) Actisorb® activated charcoal, (B) two cinnamon powders from different sources, FV (Ceylon cinnamon) and FI, (C) turmeric powder and (D) clove powder, which may be used in the device according to the invention. Chromatographic profiles were obtained by an analytical method coupling autosampler-controlled headspace solid-phase microextraction (HS-SPME) to gas chromatography (GC) with single-quadrupole mass spectrometry (MS) detection.

The inventors have indeed shown that cinnamon, clove and turmeric are particularly effective for tumour wounds, which are known to be particularly malodorous. More precisely, these spices, in powder form, have adsorbent properties comparable to those of activated charcoal (Actisorb®) on at least three VOCs characteristic of tumour wounds, namely DMDS, phenol and indole (FIGS. 1A, 1B, 1C). Moreover, these spices have olfactory properties, and notably VOCs, capable of masking VOCs which may persist and be the source of foul-smelling emanations. Such VOCs are absent in activated charcoal-based devices (FIGS. 2A, 2B, 2C, 2D), making these spices more effective in solving malodour-related problems.

According to the invention, the spice powder used is preferably capable of adsorbing at least 20%, 30%, 40%, preferably at least 50%, more preferably at least 60% of at least one of the three VOCs among DMDS, phenol and indole, and at least 20%, 30%, preferably at least 40% of the other two VOCs.

Alternatively, the spice powder is capable of adsorbing at least 20%, 30%, 40%, preferably at least 50% of the three VOCs, DMDS, phenol and indole.

In one embodiment, the spice powder used is cinnamon powder capable of adsorbing at least 20%, 30%, 40%, preferably at least 50% of at least one of the three VOCs among DMDS, phenol and indole, and at least 20%, 30%, preferably at least 40% of the other two VOCs.

In another embodiment, the spice powder used is cinnamon powder capable of adsorbing at least 65% of at least one of the three VOCs among DMDS, phenol and indole, and at least 75% of the other two VOCs.

In another embodiment, the spice powder used is cinnamon powder capable of adsorbing at least 20%, 30%, 40%, preferably at least 50% of the three VOCs: DMDS, phenol and indole.

In one embodiment, the particulate filler in the device according to the invention comprises or consists of Ceylon cinnamon (*Cinnamomum verum* or *Cinnamomum zeylanicum*), of the family Lauraceae. Such a cinnamon is commercially available. It is also possible to use Chinese cinnamon (*Cinnamomum aromaticum*), Vietnamese or Saigon (also called Cochinchina) cinnamon (*Cinnamomum loureiroi*), Indonesian cinnamon (*Cinnamomum burmannii*) or Indian cinnamon (*Cinnamomum tamala*).

In a particular embodiment, the particulate filler in the device according to the invention comprises or consists of cinnamon powder releasing at least the VOC (E)-cinnamaldehyde. In another particular embodiment, the cinnamon powder used as particulate filler releases at least the VOC (E)-cinnamaldehyde and at least one VOC among α-copaene, γ-muurolene, α-muurolene, α-selinene, δ-cadinene, sativene, α-bergamotene, D-germacrene, preferably at least one VOC among α-copaene, γ-muurolene, α-muurolene and δ-cadinene. In a preferred embodiment, the cinnamon powder used as particulate filler releases at least the VOCs (E)-cinnamaldehyde and γ-muurolene, α-muurolene. In another preferred embodiment, the cinnamon powder used as particulate filler releases at least the VOCs (E)-cinnamaldehyde and α-copaene. The presence of these VOCs may easily be verified by chromatography, notably gas chromatography. In a particular embodiment, the cinnamon powder used has a chromatographic profile similar or identical to one of the profiles in FIG. 2B.

In a particular embodiment, the cinnamon powder used releases at least the VOCs (E)-cinnamaldehyde and α-copaene, with a peak area obtained according to the method described in Example 1 greater than $100 \times 10^6$ for (E)-cinnamaldehyde and/or greater than $30 \times 10^6$ for α-copaene, preferably a peak area greater than $200 \times 10^6$ for (E)-cinnamaldehyde and/or a peak area greater than $60 \times 10^6$ for α-copaene, even more preferably a peak area greater than $350 \times 10^6$ for (E)-cinnamaldehyde and/or a peak area greater than $90 \times 10^6$ for α-copaene.

Similarly, the invention also relates to a dressing comprising a particulate filler based on turmeric, and notably on *Curcuma longa*, of the family Zingiberaceae. Turmeric is a spice already used in the medical field, and notably in topical applications, for its anti-inflammatory action. The inventors have shown that turmeric powder is also capable of adsorbing odours when used in a device comprising an absorbent layer intended to be in contact with the source from which the bad odours emanate and an adsorbent layer the particulate filler of which, which is not in direct contact with the source of the malodours, comprises turmeric powder.

In one embodiment, the turmeric is *Curcuma longa*. Such a turmeric is commercially available. In a particular embodiment, the particulate filler in the device according to the invention comprises or consists of turmeric powder releasing at least the VOC curcumene or the VOC turmerone. Preferably, the turmeric powder used releases at least the VOCs curcumene and turmerone. The presence of these VOCs may easily be verified by chromatography, notably gas chromatography. In a particular embodiment, the turmeric powder used has a chromatographic profile similar or identical to the profile in FIG. 2C.

Similarly, the invention also relates to a dressing comprising a particulate filler based on clove. In a particular embodiment, the particulate filler in the device according to the invention comprises or consists of clove powder releasing at least the VOC eugenol. The presence of this VOC may easily be verified by chromatography, notably gas chromatography. In a particular embodiment, the clove powder used has a chromatographic profile similar or identical to the profile in FIG. 2D.

The invention also relates to the use of cinnamon, turmeric or clove, as described above, more particularly in powder form, as adsorbent in a device for adsorbing odours, especially body odours. Likewise, the invention relates to the use of an adsorbent layer comprising a material permeable to volatile organic compounds (VOCs) and an adsorbent particulate filler comprising at least cinnamon, turmeric or clove, as described above, for adsorbing odours, especially body odours. Such uses are of particular interest in the medical and paramedical field, notably in a medical device such as a dressing. Likewise, the spice powder according to the invention can be used in surgical masks or anti-odour masks. Such masks may be designed directly from an adsorbent layer according to the invention, incorporating a spice powder such as cinnamon, turmeric or clove.

EXAMPLES

Example 1

Comparison of the Adsorbent Properties of Activated Charcoal (Actisorb®), Cinnamon, Turmeric and Clove (Powder)

In order to evaluate the adsorbent properties of cinnamon (Ceylon cinnamon—FV), turmeric (*Curcuma longa*) and clove, the adsorption profiles on three VOCs characteristic of malodorous necroses, namely dimethyl disulphide (DMDS—$C_2H_6S_2$), phenol (Ph- $C_6H_6O$) and indole (In—$C_8H_7N$), were studied, in comparison with the adsorption profile of activated charcoal which is traditionally used to mask odours emanating from such necroses.

At the same time, the adsorbent properties of three cinnamons from different sources (FV), (FC) and (FI) were compared by studying the adsorption profiles on these same three VOCs, in comparison with the adsorption profile of activated charcoal.

Materials & Methods

The composition of the test solution T3C, with the three VOCs characteristic of malodorous necroses, is as follows: pure water containing 50 mg/L dimethyl disulphide (DMDS), 125 mg/L phenol (Ph) and 500 mg/L indole (In). The pure compounds for the preparation of the solution come from Sigma-Aldrich (Saint-Quentin Fallavier, France).

The sample vials (round glass, inner diameter 22 mm and height 75 mm, closed tightly with a screw cap with silicone seal) are prepared as follows: at the bottom of the vial a cellulose matrix (14 mm×14 mm square, 100 mg) on which is deposited a 20 µL volume of the solution T3C (i.e. 1µg DMDS, 2.5 µg Ph and 10 µg In) which then soaks the cellulose matrix, then covered with Aquacel® polyurethane film (1.8 cm diameter, 40 mg) and finally placement of a square of cellulose (16 mm×16 mm, 130 mg) containing between its wefts 30 mg of activated charcoal (Actisorb®) or 30 mg of cinnamon powder with an average particle size of 75 µm, (1(FV)/2(FC)/3(FI)) or 30 mg of turmeric powder with an average particle size of 90 µm (*Curcuma longa*) or 30 mg of clove powder with an average particle size of 820 µm (*Fyzygium aromaticum*, or clove tree). A control vial, the reference, is also prepared in the same way but containing neither activated charcoal nor spice.

The analysis method used combines autosampler-controlled headspace solid-phase microextraction (HS-SPME) with gas chromatography (GC) with single-quadrupole mass spectrometry (MS) detection.

The SPME fibre used is a carboxen-polydimethylsiloxane (CAR-PDMS) fibre, 10 mm in length and 75 µm in thickness, from Supelco (Sigma-Aldrich, Saint-Quentin Fallavier, France).

The chromatograph and the mass spectrometer are the models GC 7890A and 5975C XL MSD, respectively, from Agilent Technologies (Les Ulis, France).

The autosampler coupled to the chromatograph is a Gerstel MPS Autosampler (RIC, Saint-Priest, France).

Operating conditions: the vial is incubated for 6 min at 40° C. and then extraction in the vial headspace is performed for 30 min, also at 40° C. Desorption occurs in the GC injector at 280° C. in splitless mode for 10 min Separation is performed on a DB5-MS column, containing a polydimethylsiloxane film (95% methyl, 5% phenyl), dimensions 30 m×0.25 mm with a film thickness of 1 µm. The carrier gas is helium with a constant column output flow rate of 1.0 mL/min. The temperature programme of the column is 40° C. with holding time 2 min, then at 7° C./min up to 300° C. and holding time 1 min (analysis time 40.14 min).

For spectrometric detection, the temperatures are: for the transfer line 280° C., the source 230° C. and the quad 150° C. Ionization is performed in the electron impact (EI) mode at 70 eV. Two detection modes are used, the SCAN (progressive scan) mode between m/z 25 to 300 and the SIM (Selected Ion Monitoring) mode for m/z 94 (DMDS and Ph targets) and 117 (In target).

The compounds are identified by comparing experimental mass spectra (taken under the chromatographic elution peak) with those of the National Institute of Standards and Technology library (NIST, version 2.0f, rev.2010).

The elution peaks of the compounds on the chromatogram are characterized by their retention time given in minutes and taken at the peak maximum, and by their area (surface area under the peak envelope) given in arbitrary area units (represents a number of counts).

Results

As shown in FIG. 1 and summarized in Table 1 below, the VOC adsorption rate by activated charcoal (Actisorb®) is greater than 92% Cinnamon, in turn, has an adsorption rate comprised between 80 and 92% depending on the VOCs, confirming the malodour-adsorbing properties of this spice. Likewise, the adsorption rates are between 67 and 90% for clove and between 41 and 62% for turmeric.

In Tables 1 and 2, the peak areas are given in area units. The control tube represents the reference in terms of the emitted amounts of VOCs concerned in the tube. The adsorption rate is calculated as follows: adsorption rate= [(control tube VOC peak area)−(spice tube VOC peak area)]/(control tube VOC peak area).

TABLE 1

Adsorption rate of dimethyl disulphide (DMDS), phenol (Ph) and indole (In) per 30 mg of activated charcoal (Actisorb ®) or cinnamon (Ceylon cinnamon - FV) or turmeric or clove (powder).

| VOC (m/z fragment for SIM detection) | VOC retention time (min) | Control Area (×10$^6$) in Area Units (AU) | Actisorb ® Area (×10$^6$) % adsorbed | Cinnamon FV Area (×10$^6$) % adsorbed | Turmeric Area (×10$^6$) % adsorbed | Clove Area (×10$^6$) % adsorbed |
|---|---|---|---|---|---|---|
| DMDS (m/z = 94) | 10.05 | 118.7 | 0.5 99.6% | 9.1 92.3% | 44.7 62.3% | 11.4 90.4% |
| Ph (m/z = 94) | 16.14 | 88.2 | 5.7 93.5% | 17.6 80.0% | 47.7 45.9% | 27.9 68.4% |
| In (m/z = 117) | 24.03 | 83.1 | 6.3 92.4% | 10.5 87.4% | 48.3 41.9% | 27.4 67.0% |

Control: 3VOCs; Actisorb ®: 3VOCs + 30 mg activated charcoal;

cinnamon: 3VOCs + 30 mg cinnamon powder;

turmeric: 3VOCs + 30 mg turmeric powder;

clove: 3VOCs + 30 mg clove powder

TABLE 2

Adsorption rate of dimethyl disulphide (DMDS), phenol (Ph) and indole (In) per 30 mg of activated charcoal (Actisorb ®) or various powdered cinnamons (FV, FC and FI).

| VOC retention time (min) | VOC (m/z fragment for SIM detection) | Control Area (×10$^6$) in AU | Actisorb Area (×10$^6$) % adsorbed | Ceylon cinnamon (FV) Area (×10$^6$) % adsorbed | Cinnamon FC Area (×10$^6$) % adsorbed | Cinnamon FI Area (×10$^6$) % adsorbed |
|---|---|---|---|---|---|---|
| 10.00 | DMDS (m/z = 94) | 19.92 | 0.10 99% | 5.99 70% | 6.26 69% | 3.97 80% |
| 16.10 | Ph (m/z = 94) | 12.34 | 0.09 99% | 2.89 77% | 3.07 75% | 3.32 73% |
| 23.97 | In (m/z = 117) | 14.05 | 0.11 99% | 1.52 89% | 3.57 75% | 2.27 84% |

Example 2

Study of VOCs Present in Cinnamon, Turmeric and Clove

As shown above, spice powders have a slightly lower adsorbent capacity than Actisorb® activated charcoal with respect to dimethyl disulphide, phenol and indole. However, on a panel of users, it is the devices according to the invention, comprising a cinnamon-based particulate filler, that achieve a higher satisfaction rate (see Example 3 below). Indeed, the fragrant spices have VOCs capable of at least partially masking other VOCs, and notably VOCs likely to emanate from foul-smelling wounds.

The combination, according to the invention, of the adsorbent and fragrant properties of the spice powders used potentiates the effects of the device and is completely satisfactory for eliminating bad odours.

In order to determine which VOCs present in cinnamon, turmeric and clove (powder) are able to mask bad odours, an analysis of VOCs from cinnamon (Ceylon cinnamon), turmeric (*Curcuma longa*), clove (*Fyzygium aromaticum*, or clove tree) and activated charcoal (Actisorb®) was performed. To that end, vials were prepared, each directly containing 30 mg of cinnamon (FV and FI), 30 mg of turmeric, 30 mg of clove powder or 30 mg of Actisorb®. The vials were then characterized using the same analytical method as presented in Example 1 (exactly identical operating conditions).

Results

As seen in FIG. 2 and summarized in Table 3 below, activated charcoal does not release any VOCs (FIG. 2A). Conversely, the cinnamons (FIG. 2B), like turmeric (FIG. 2C) and clove (FIG. 2D), release many VOCs.

The masking aspect of fragrant spices, which allows the spices not only to adsorb bad odours but also to cover them, may thus be explained by the presence of VOCs, totally absent from Actisorb®, some of which are likely to have a strong effect on sensory perception. This is the case, for example, of (E)-cinnamaldehyde for cinnamon, of curcumene and turmerone for turmeric, or of eugenol for clove.

TABLE 3

Comparative analysis of VOCs present in cinnamon (Ceylon cinnamon - FV), turmeric (*Curcuma longa*), clove and activated charcoal (Actisorb ®)

| Retention time (min) | Name (CAS number) | Molecular formula (molar mass - g/mol) | Area of the peak if present (in Area Units ×10$^6$) | | | |
|---|---|---|---|---|---|---|
| | | | Actisorb ® | Cinnamon FV | Turmeric | Clove |
| 17.65 | p-Cymene (99-87-6) | $C_{10}H_{14}$ (134) | no | no | 41 | no |
| 17.78 | D-Limonene (5989-27-5) | $C_{10}H_{16}$ (136) | no | 49 | 67 | no |
| 17.98 | Eucalyptol (470-82-6) | $C_{10}H_{18}O$ (154) | no | no | 30 | no |
| 20.93 | Camphor (76-22-2) | $C_{10}H_{16}O$ (152) | no | 37 | 61 | no |
| 21.78 | Methyl salicylate (or Analgit) (119-36-8) | $C_8H_8O_3$ (152) | no | no | no | 128 |
| 23.66 | (E)-Cinnamaldehyde (14371-10-9) | $C_9H_8O$ (132) | no | 1660 | no | no |
| 25.40 | Eugenol (97-53-0) | $C_{10}H_{12}O_2$ (164) | no | no | no | 9059 |
| 25.76 | α-Copaene (3856-25-5) | $C_{15}H_{24}$ (204) | no | 3384 | no | 323 |
| 26.14 | (E)-Isoeugenol (5932-68-3) | $C_{10}H_{12}O_2$ (164) | no | no | no | 98 |
| 26.29 | (+)-Sativene (3650-28-0) | $C_{15}H_{24}$ (204) | no | 44 | no | no |
| 26.60 | α-Bergamotene (17699-05-7) | $C_{15}H_{24}$ (204) | no | 87 | no | no |
| 26.83 | Caryophyllene (87-44-5) | $C_{15}H_{24}$ (204) | no | 120 | no | 4370 |

TABLE 3-continued

Comparative analysis of VOCs present in cinnamon (Ceylon cinnamon - FV), turmeric (*Curcuma longa*), clove and activated charcoal (Actisorb ®)

| Retention time (min) | Name (CAS number) | Molecular formula (molar mass - g/mol) | Area of the peak if present (in Area Units ×$10^6$) | | | |
|---|---|---|---|---|---|---|
| | | | Actisorb ® | Cinnamon FV | Turmeric | Clove |
| 26.85 | D-Germacrene (23986-74-5) | $C_{15}H_{24}$ (204) | no | 46 | no | no |
| 27.40 | α-Humulene (or α-Caryophyllene) (6753-98-6) | $C_{15}H_{24}$ (204) | no | 205 | no | 833 |
| 27.43 | α-Curcumene (644-30-4) | $C_{15}H_{22}$ (202) | no | no | 862 | no |
| 27.57 | γ-Muurolene (30021-74-0) | $C_{15}H_{24}$ (204) | no | 437 | no | 108 |
| 27.63 | α-Zingiberene (495-60-3) | $C_{15}H_{24}$ (204) | no | no | 162 | no |
| 27.86 | Aceteugenol (93-28-7) | $C_{12}H_{14}O_3$ (206) | no | no | no | 149 |
| 27.89 | α-Himachalene (3853-83-6) | $C_{15}H_{24}$ (204) | no | no | 124 | no |
| 27.96 | α-Muurolene (31983-22-9) | $C_{15}H_{24}$ (204) | no | 544 | no | no |
| 28.05 | β-Selinene (17066-67-0) | $C_{15}H_{24}$ (204) | no | 41 | no | no |
| 28.12 | α-Selinene (473-13-2) | $C_{15}H_{24}$ (204) | no | 74 | no | no |
| 28.24 | β-Sesquiphellandrene (20307-83-9) | $C_{15}H_{24}$ (204) | no | no | 277 | no |
| 28.28 | δ-Cadinene (483-76-1) | $C_{15}H_{24}$ (204) | no | 908 | no | 179 |
| 28.45 | (−)-Calamene (483-77-2) | $C_{15}H_{22}$ (202) | no | 646 | no | no |
| 28.62 | Isolongifolene, 4,5,9,10-dehydro (156747-45-4) | $C_{15}H_{20}$ (200) | no | 167 | no | no |
| 28.86 | α-Calacorene (21391-99-1) | $C_{15}H_{20}$ (200) | no | 132 | no | no |
| 29.64 | Turmerone (180315-67-7) | $C_{15}H_{22}O$ (218) | no | no | 82 | no |
| 30.38 | Cubenol (21284-22-0) | $C_{15}H_{26}O$ (222) | no | 45 | no | no |
| 30.63 | α-Cadinol (481-34-5) | $C_{15}H_{26}O$ (222) | no | 48 | no | no |
| 30.70 | β-Turmerone (82508-14-3) | $C_{15}H_{22}O$ (218) | no | no | 841 | no |
| 30.78 | AR-Turmerone (532-65-0) | $C_{15}H_{20}O$ (216) | no | no | 167 | no |
| 31.13 | Cadalene (483-78-3) | $C_{15}H_{18}$ (198) | no | 37 | no | no |
| 31.37 | α-Turmerone (82508-15-4) | $C_{15}H_{22}O$ (218) | no | no | 225 | no | no = not observed
Cinnamons from different origins (FV, FC, FI, W) were also analysed in order to identify characteristic VOCs.

TABLE 4

Comparative analysis of VOCs present in various cinnamons

| RT (min) | Name (CAS number) | Molecular formula | MW (g/mol) | Area (×$10^6$) in Area Units | | | |
|---|---|---|---|---|---|---|---|
| | | | | Cinnamon FV (Ceylon cinnamon) | Cinnamon FC | Cinnamon FI | Cinnamon W |
| 19.30 | L-Linalool (78-70-6) | $C_{10}H_{18}O$ | 154 | nd | trace | 30 | 118 |
| 23.63 | (E)-Cinnamaldehyde (14371-10-9) | $C_9H_8O$ | 132 | 88 | 658 | 656 | 367 |
| 25.83 | α-Copaene (3856-25-5) | $C_{15}H_{24}$ | 204 | 1431 | 62 | 726 | 117 |

TABLE 4-continued

Comparative analysis of VOCs present in various cinnamons

| | | | | Area (×10⁶) in Area Units | | | |
|---|---|---|---|---|---|---|---|
| RT (min) | Name (CAS number) | Molecular formula | MW (g/mol) | Cinnamon FV (Ceylon cinnamon) | Cinnamon FC | Cinnamon FI | Cinnamon W |
| 26.81 | β-Caryophyllene (87-44-5) | $C_{15}H_{24}$ | 204 | 8 | 3 | 307 | 948 |
| 27.63 | γ-Muurolene (30021-74-0) | $C_{15}H_{24}$ | 204 | 79 | 9 | 32 | nd |
| 28.03 | α-Muurolene (31983-22-9) | $C_{15}H_{24}$ | 204 | 103 | 28 | 79 | 2 |
| 28.37 | δ-Cadinene (483-76-1) | $C_{15}H_{24}$ | 204 | 165 | 35 | 86 | 5 |
| 28.51 | (−)-Calamene (483-77-2) | $C_{15}H_{22}$ | 202 | 142 | 27 | 61 | 6 | nd = not detected

It can be seen that these various cinnamons have a peak area for (E)-cinnamaldehyde greater than 350×10⁶ and/or a peak area for α-copaene greater than 100×10⁶.

Example 3

Sensory Perception

The adsorbent and masking properties of cinnamon (Ceylon cinnamon—FV) and of activated charcoal were evaluated and compared by blind testing on a panel of users on odours emitted by Maroilles cheese. At the same time, the adsorbent and masking properties of various cinnamons (FV, FC, FI and W) were compared, also by blind testing on this panel of users on odours emitted by Maroilles cheese.

Indeed, according to the analysis of JP Dumont (JP Dumont et al., Le Lait/January-February 1974/No. 531-532, "Etude des composes volatils neutres presents dans les fromages à pâte molle et à croute lavée" ["Study of neutral volatile compounds present in soft and washed-rind cheeses"]), the smell of Maroilles is substantially similar to that of tumour wounds. Table 3 below summarizes the main VOCs released by tumour wounds and by Maroilles. The VOCs released by tumour wounds were obtained by gas chromatographic analysis (same analytical method as in Example 1) of three samples of necrosis (necroses taken from malodorous tumour wounds).

TABLE 5

Main VOCs common to Maroilles and tumour wounds

| Compounds | Maroilles | Tumour wounds | Sensory perception |
|---|---|---|---|
| 3-Methyl-1-butanol/ Butanoic acid | + + | + + + | Strong goat cheese smell |
| Dimethyl disulphide | + + | + + + | Rotten garlic smell |
| Ethyl acetate/ Acetic acid | + + + | + + + | Vinegar smell |
| Acetophenone/phenol | + + + + | + + | Tar smell |
| Indole | + + + + | + + + + | Intense faecal matter smell |

Materials & Methods

The study was conducted within Institut Curie. The 16 participants in the study are Institut Curie caregivers, doctors and researchers.

The main objective was to determine the best condition(s) for reducing the perception of malodours using cinnamon powder.

The hedonic nature of the samples was assessed on a scale from 1 (very unpleasant) to 5 (very pleasant), with 3 being neutral. The perceived odours were also described by the adjectives: "heavy/strong/sticky/aromatic/disgusting/disturbing/pleasant/mild", and associated with the adjectives as "cadaverous/putrid/urinous/excremental/vegetable/foul" (multiple response possible).

SAMPLES

The samples each comprised 6 g of Maroilles per 1 g of spice or Actisorb®. The control consisted of 6 g of Maroilles, alone.

These samples were placed in glass jars wrapped in aluminium foil for at least 20-30 min before the test, so that the odours of the samples would disperse in the air inside the jars and allow an effective sensory evaluation.

Study Protocol:

The participants were informed of the unpleasant nature of the samples so as to avoid a surprise or restraint effect, and thus maintain continuous inhalation.

The tests were performed blind. The participants did not know the content of the samples. The samples were presented to each of the participants.

A "nose rinse" was systematically performed between two evaluations. The nose rinse was performed by sniffing a jar containing water or sniffing one's own skin (wrist or elbow).

The perception study was conducted kinetically to evaluate the effectiveness of the compounds on malodorous VOCs. The kinetic times were T0, T24 and T48 (in hours).

The statistical analysis was performed with the help of Prof. C. Dacremont, Centre for Taste and Feeding Behaviour, CNRS-INRA—University of Burgundy—AgroSup Dijon.

Results

Figure 3:
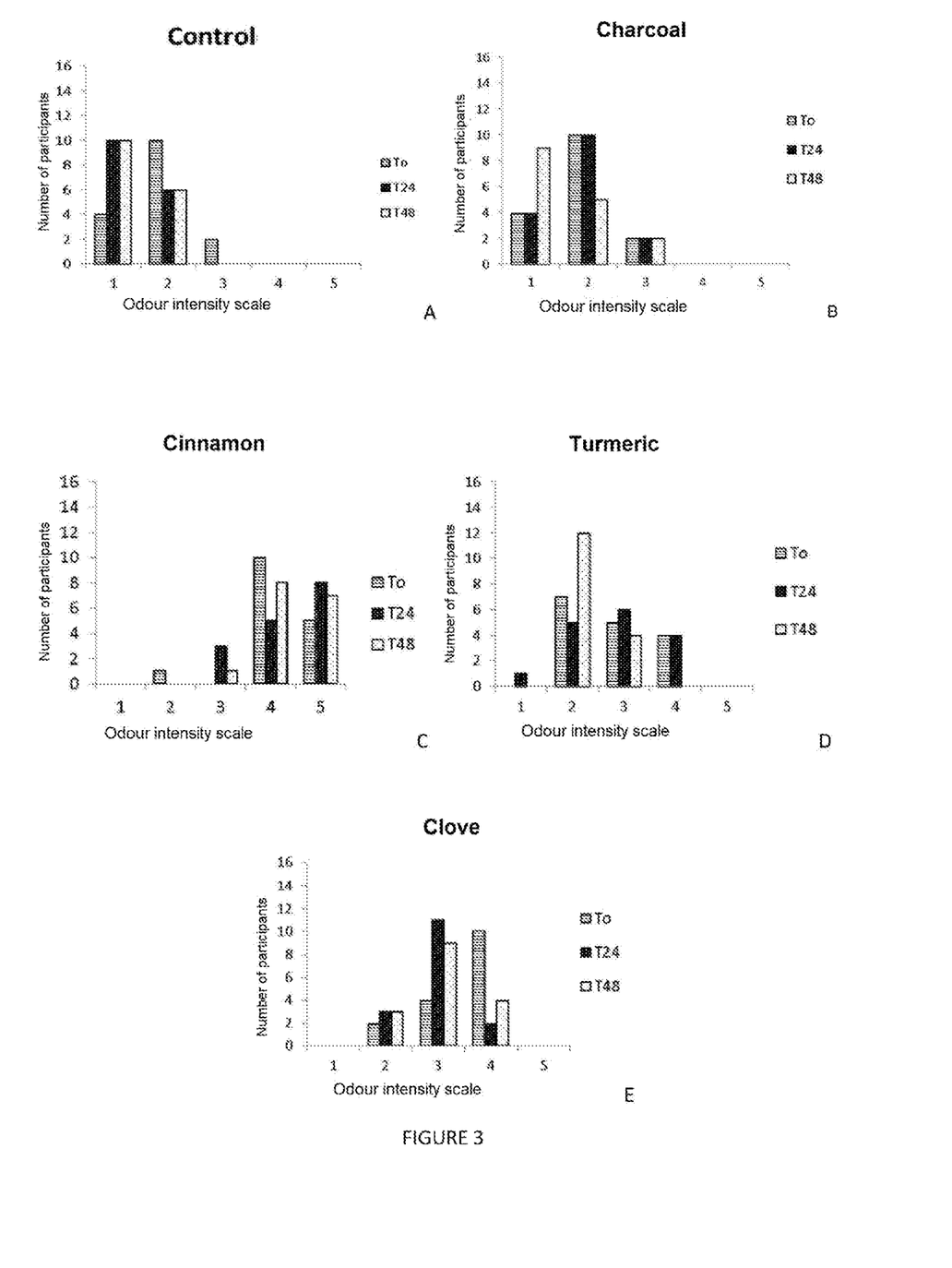
FIG. 3: Blind sensory testing on a panel of users to assess odour intensity associated with malodorous VOCs: (A) Control; (B) activated charcoal (Actisorb®); (C) cinnamon (Ceylon cinnamon) powder; (D) turmeric (*Curcuma longa*) powder; (E) clove powder at T0, T24 hours and T48 hours after application to Maroilles cheese.

The majority of participants regarded the odours emanating from the control samples (Maroilles alone) and the Actisorb® samples (Maroilles+Actisorb®) as unpleasant (2) to very unpleasant (1). More precisely, 68% of the participants associate the control sample as very unpleasant and 53% associate the sample containing Actisorb® as unpleasant (FIGS. 3A and 3B).

In contrast, the majority of participants regarded the odours emanating from the samples containing the spices as neutral (3), pleasant (4) or very pleasant (5). In particular, 40% of the participants associated the cinnamon sample as pleasant, and 18% for turmeric. (FIGS. 3C, 3D and 3E).

Figure 4:
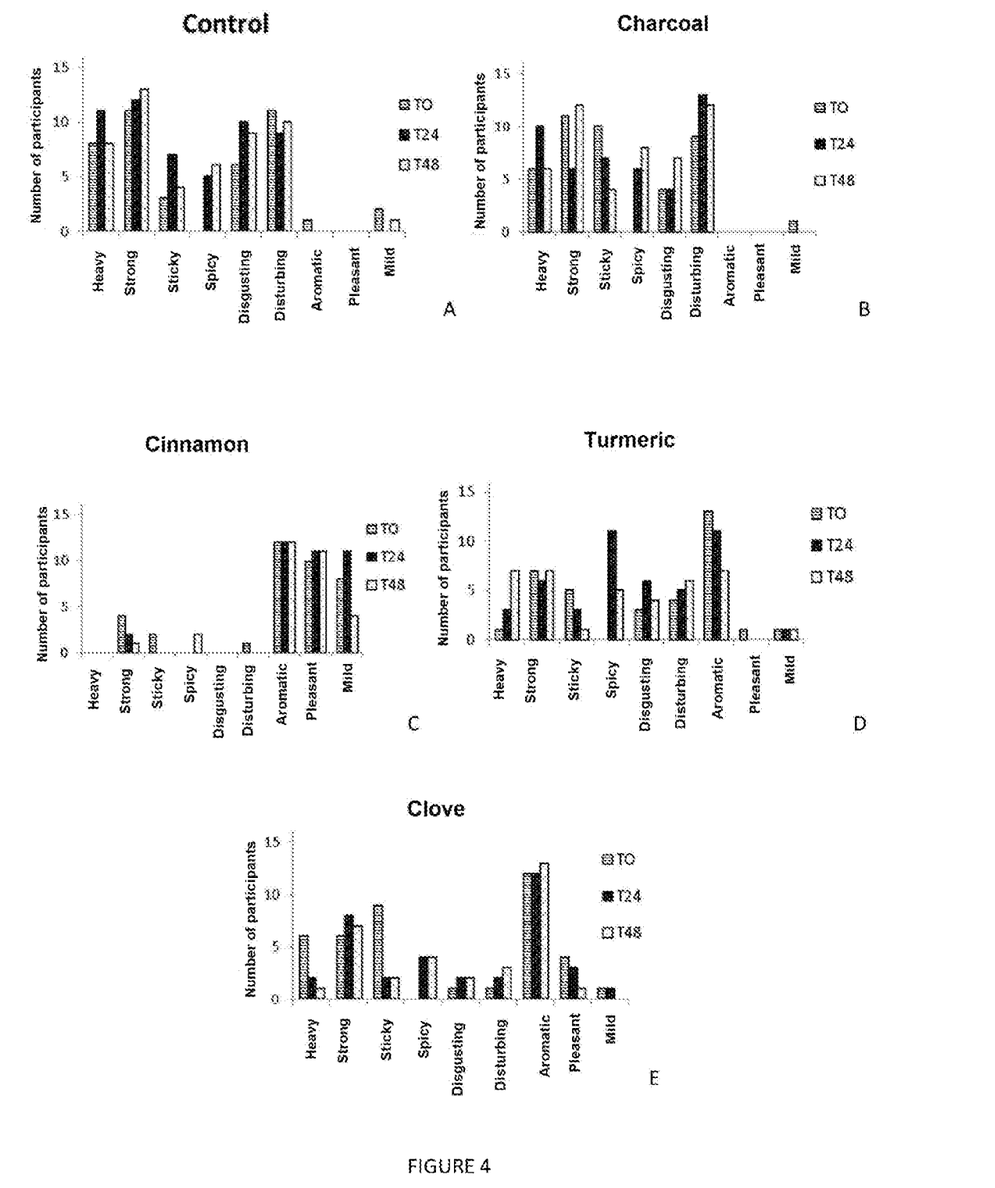
FIG. 4: Blind sensory testing on a panel of users to describe the odour associated with malodorous VOCs: (A) Control; (B) activated charcoal (Actisorb®); (C) cinnamon (Ceylon cinnamon) powder; (D) turmeric (*Curcuma longa*) powder; (E) clove powder at T0, T24 hours and T48 hours after application to Maroilles cheese.
Figure 5:
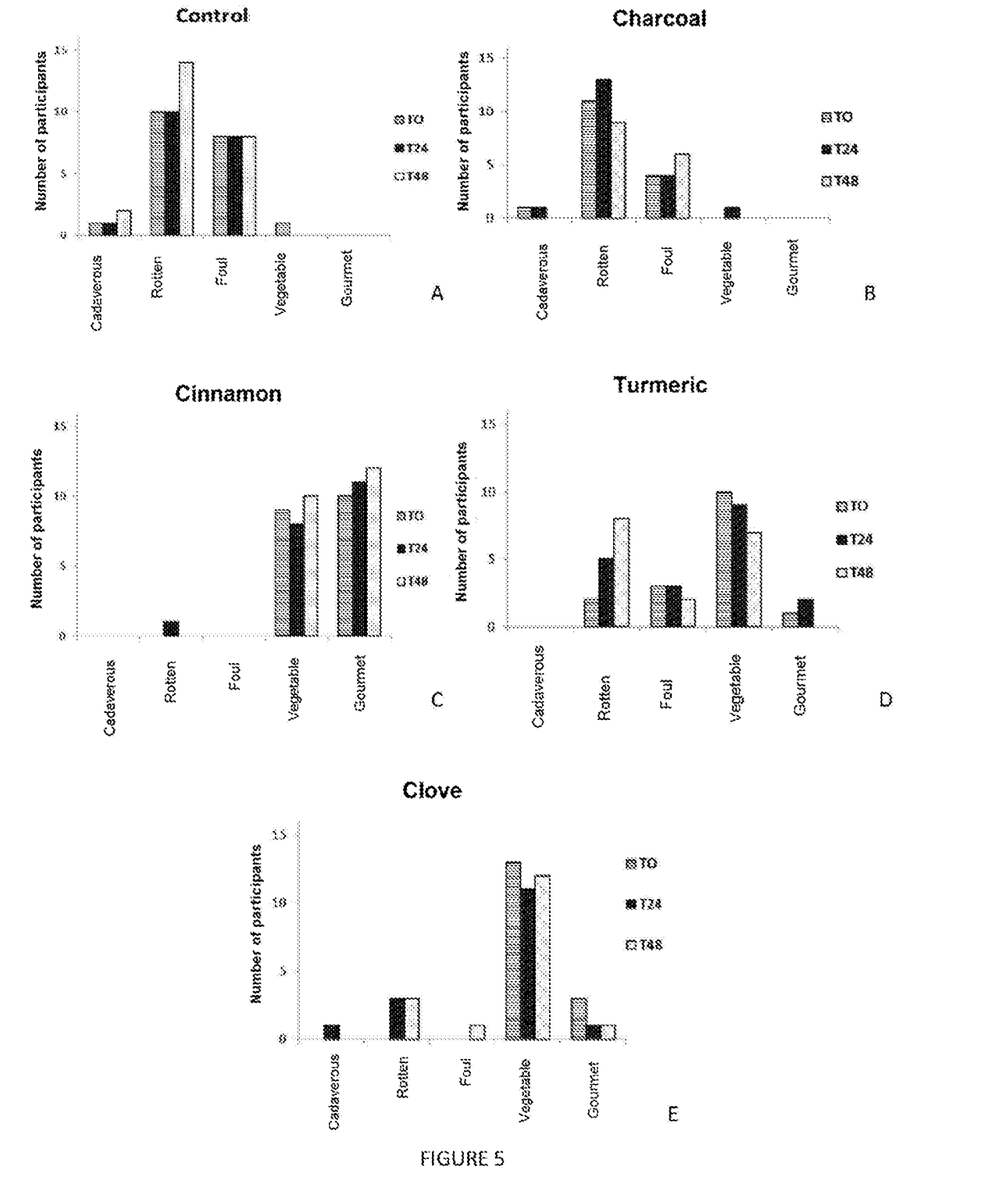
FIG. 5: Blind sensory testing on a panel of users of association of the odour associated with malodorous VOCs: (A) Control; (B) activated charcoal (Actisorb®); (C) cinnamon (Ceylon cinnamon) powder; (D) turmeric (*Curcuma longa*) powder; (E) clove powder at T0, T24 hours and T48 hours after application to Maroilles cheese.

The odours emanating from the samples containing the spices were mainly described as being aromatic and pleasant. In contrast, the odours emanating from the control samples such as the samples containing Actisorb® or the control were described as disgusting, disturbing and strong (FIG. 4). Similarly, while many participants associated the odour emanating from the samples containing a spice with a "vegetable" or "gourmet" odour, the qualifiers used for the odours emanating from the control sample and from the Actisorb® sample are mostly "rotten" and "foul" (FIG. 5).

Figure 6:
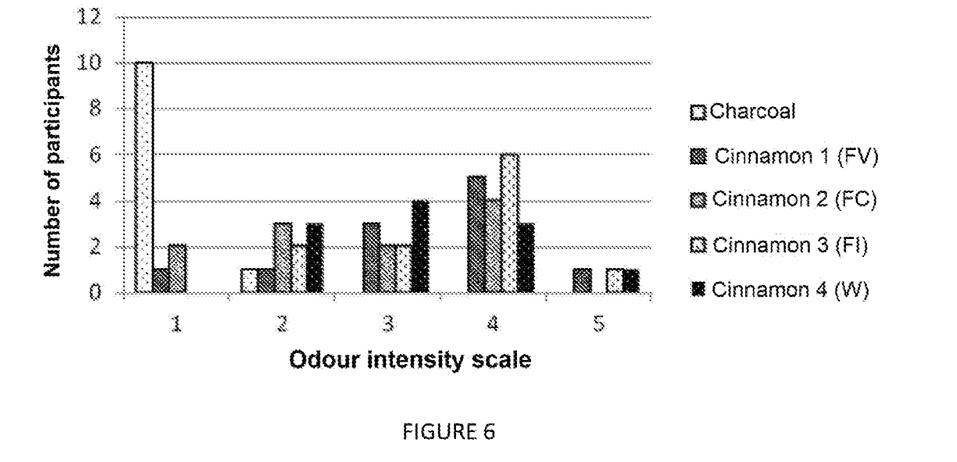
FIG. 6: Blind sensory testing on a panel of users to assess odour intensity associated with malodorous VOCs at T0, T24 hours and T48 hours after application of activated charcoal (Actisorb®) or various cinnamon powders (FV, FC, FI and W) to Maroilles cheese.

The sensory tests performed with the various cinnamons were all satisfactory (FIG. 6). The majority of participants regarded the odours emanating from the samples containing the cinnamons as neutral (3), pleasant (4) or very pleasant (5).

These sensory tests confirm that the spices used have a high capacity to adsorb and mask VOCs, and especially VOCs perceived as unpleasant by users. In contrast, activated charcoal is unable to satisfactorily adsorb and mask these same VOCs, which continue to be perceived as unpleasant and/or annoying by users.

The invention claimed is:

1. A device for adsorbing odours comprising an absorbent layer and an adsorbent layer, said adsorbent layer being provided with a material permeable to volatile organic compounds (VOCs) and an adsorbent particulate filler comprising at least one spice, wherein the material permeable to VOCs is a woven or nonwoven fabric and the at least one spice is maintained in powder form within the material permeable to VOCs.

2. The device for adsorbing odours according to claim 1, wherein the at least one spice is selected from cinnamon, turmeric and clove.

3. The device for adsorbing odours according to claim 1, wherein the odours are body odours.

4. The device for adsorbing odours according to claim 1, wherein the adsorbent particulate filler has an average particle size comprised between 700 and 900 µm.

5. The device for adsorbing odours according to claim 1, comprising between 00.5 and 5 g of spices per 100 $cm^2$ of the material permeable to VOCs.

6. The device for adsorbing odours according to claim 1, wherein the material permeable to VOCs is selected from nylon, cotton, linen, viscose, polyethylene, polypropylene, and polyester.

7. The device for adsorbing odours according to claim 1, wherein the material permeable to VOCs has geometric shapes in which the adsorbent particulate filler is able to be contained.

8. The device for adsorbing odours according to claim 1, wherein the absorbent layer comprises at least one permeable or semipermeable material.

9. The device for adsorbing odours according to claim 1, further comprising a protective layer sandwiched between the absorbent layer and the adsorbent layer.

10. The device for adsorbing odours according to claim 1, further comprising a second absorbent layer, wherein the adsorbent layer is sandwiched between the absorbent layer and the second absorbent layer.

11. The device for adsorbing odours according to claim 1, in the form of a dressing.

12. The device for adsorbing odours according to claim 1, in the form of a diaper, sanitary protection, absorbent pad, or panty liner.

13. The device for adsorbing odours according to claim 1, wherein the at least one spice is cinnamon.

14. The device for adsorbing odours according to claim 1, wherein the adsorbent particulate filler has an average particle size comprised between 40 and 100 µm.

15. The device for adsorbing odours according to claim 1, wherein the adsorbent particulate filler has an average particle size comprised of less than 1000 µm.

16. The device for adsorbing odours according to claim 8, wherein the at least one permeable or semi-permeable material is selected from alginates, carboxymethylcellulose (CMC), and hydrophilic cotton.

* * * * *